US00PP32785P2

(12) United States Plant Patent
Lee

(10) Patent No.: US PP32,785 P2
(45) Date of Patent: Feb. 2, 2021

(54) ***DISTYLIUM* PLANT NAMED 'BLDY02'**

(50) Latin Name: *Distylium hybrida*
Varietal Denomination: BLDY02

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 0 days.

(21) Appl. No.: 16/602,972

(22) Filed: Jan. 7, 2020

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
CPC ... A01H 5/02; A01H 5/00; A01H 6/00; A01H 6/80
See application file for complete search history.

(56) References Cited

U.S. PATENT DOCUMENTS

PP23,128 P2 * 10/2012 Dirr ..... A01H 5/02
Plt./226

OTHER PUBLICATIONS

Southern Living Plant Collection *Distylium*, retrieved on Jun. 30, 2020, retrieved from the Internet at https://southernlivingplants.com/plant/distylium/, 2 pp. (Year: 2020).*
The Landscape Show 2019, retrieved on Jun. 30, 2020, retrieved from the Internet at https://www.thelandscapeshow.org/2019/public/eBooth.aspx?BoothID=109035, 6 pp. (Year: 2019).*

* cited by examiner

*Primary Examiner* — June Hwu
(74) *Attorney, Agent, or Firm* — Cassandra Bright

(57) ABSTRACT

A new and distinct cultivar of *Distylium* plant named 'BLDY02' is disclosed, characterized by unique bronze new foliage. Foliage is dark green and glossy at maturity. Plant habit is attractive with upright branches forming a dense mound. The new cultivar is a *Distylium*, suitable for ornamental garden purposes.

2 Drawing Sheets

Latin name of the genus and species: *Distylium hybrida*.
Variety denomination: 'BLDY02'.

BACKGROUND OF THE INVENTION

The new cultivar is a product of a planned breeding program by the inventor. This new variety, hereinafter referred to as 'BLDY02', was found as the result of an open pollination conducted during 2007 which included a group of unnamed, unpatented *Distylium hybrida* plants as parents. The inventor discovered the unique seedling in Independence, La., at a research nursery during Spring of 2012.

After identifying the new variety as a potentially interesting selection, the inventor first organized propagation of 'BLDY02' by semi-hardwood cuttings during the Summer of 2015 at a nursery in Loxley, Ala. The inventor continued confidential, controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'BLDY02' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'BLDY02' These characteristics in combination distinguish 'BLDY02' as a new and distinct *Distylium* cultivar:

1. Moderate to fast growth.
2. Bronze new foliage.
3. Shiny dark green mature foliage.
4. Attractive plant shape formed by upright growth developing into a mounding plant.
5. Dense, compact growth.

COMPARISON TO PARENT VARIETY

The parent varieties are unidentified.

COMMERCIAL COMPARISON

'BLDY02' can be compared to the commercial variety *Distylium myricoides* x *racemosum* 'Vintage Jade', U.S. Plant Pat. No. 23,128. Plants of the new cultivar 'BLDY02' are similar to plants of 'Vintage Jade' in most horticultural characteristics, however, plants of the new cultivar 'BLDY02' differ in the following:

1. 'BLDY02' is a more compact plant than 'Vintage Jade'.
2. 'BLDY02' produces smaller foliage.
3. 'BLDY02' produces bronze new growth not seen on 'Vintage Jade'.

'BLDY02' can be compared to the commercial variety *Distylium hybrida* 'BLDY01', filed concurrently and having U.S. Plant application Ser. No. 16/602,971. Plants of the new cultivar 'BLDY02' are similar to plants of 'BLDY01' in most horticultural characteristics, however, plants of the new cultivar 'BLDY02' differ in the following:

1. 'BLDY02' grows approximately 30 cm shorter at maturity than 'BLDY01'.
2. 'BLDY02' produces bronze new growth not seen on 'BLDY01'.

BRIEF DESCRIPTION OF THE PHOTOGRAPHS

Figure 1:
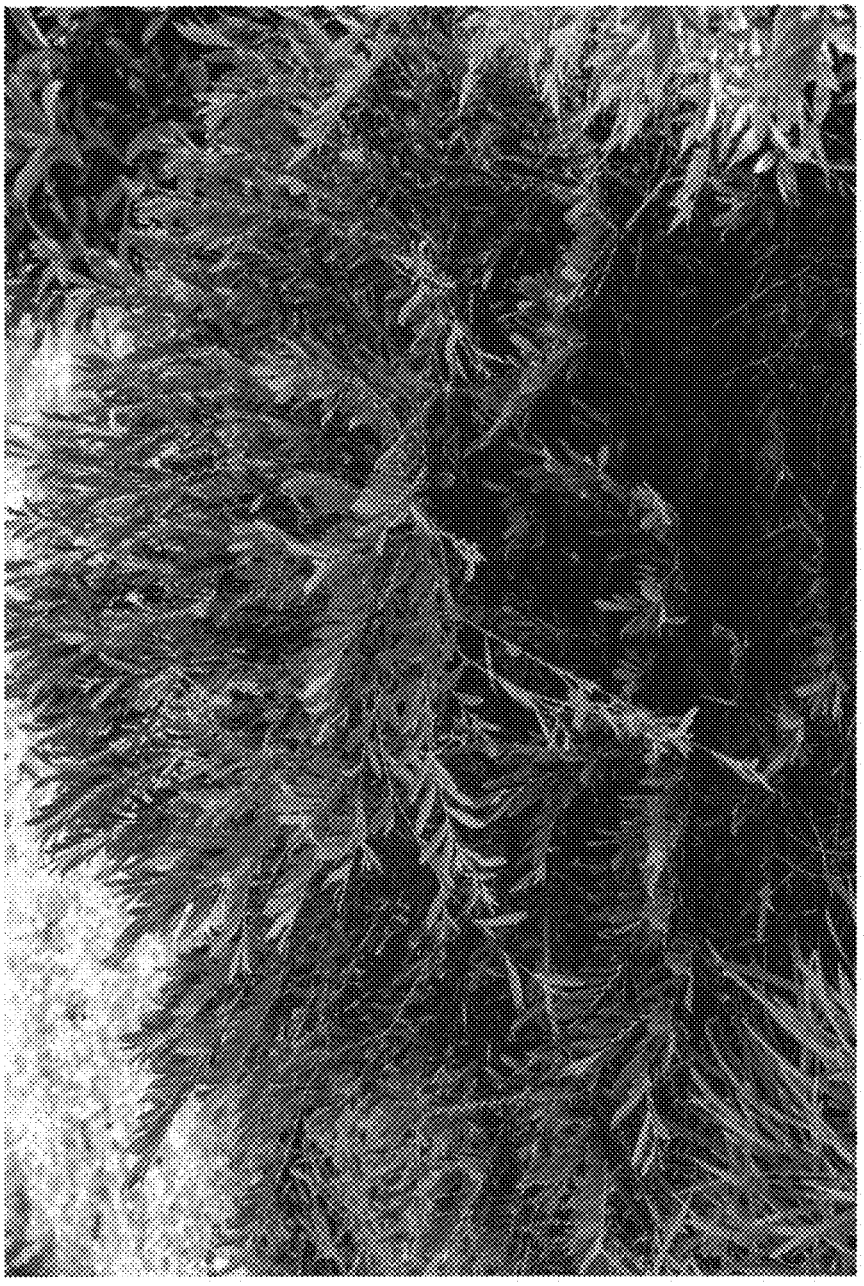

The accompanying photograph in FIG. 1 illustrates in full color a plant of 'BLDY02' grown outdoors in Alabama.

Figure 2:
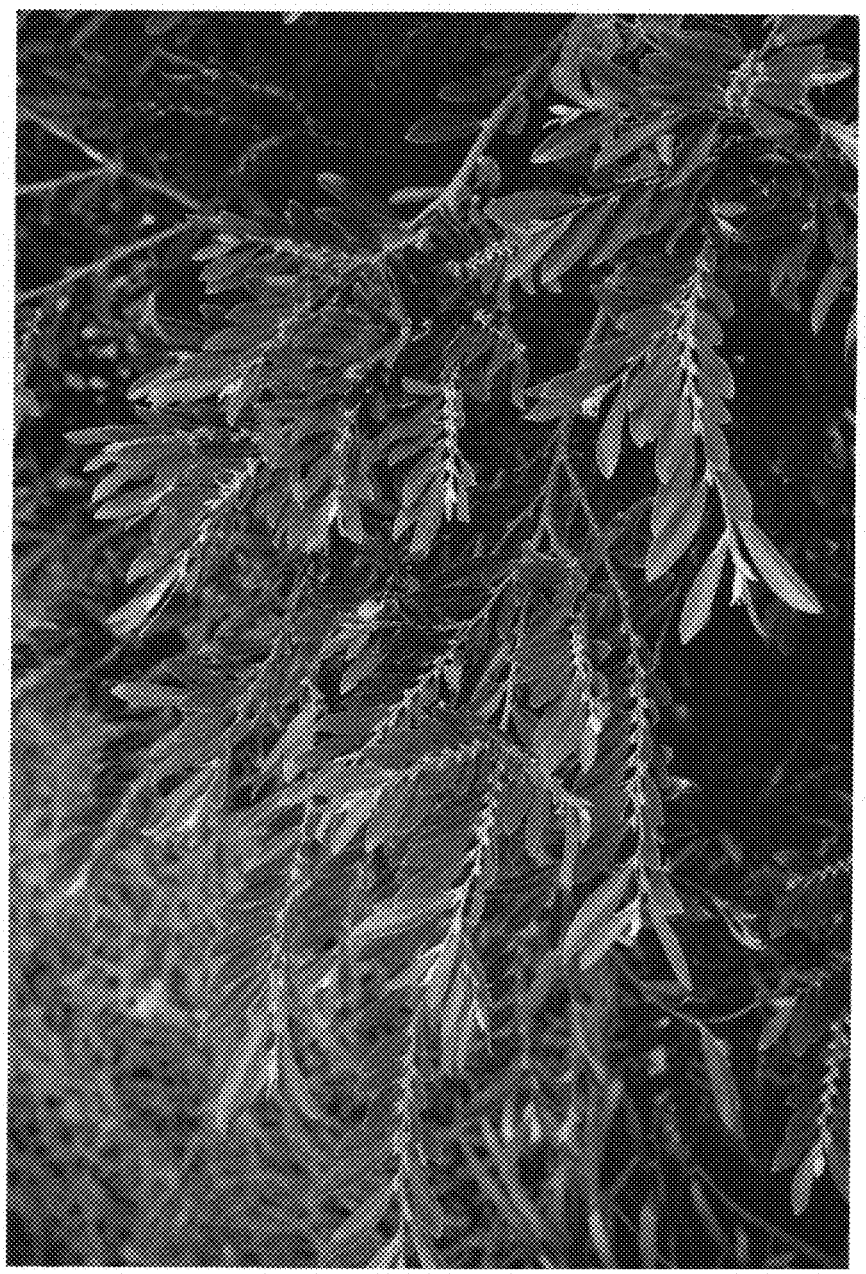

FIG. 2 shows a close up of typical foliage of the new variety. The plant is approximately 2 years old, and is shown in a three-gallon container.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BLDY02' plants grown outdoors in Loxley, Alabama. Plants are approximately 2 years old, in a 2 gallon nursery container. Measurements and numerical values represent averages of typical plant types.

Botanical classification: *Distylium hybrida* 'BLDY02'.

PROPAGATION

Typically by semi-hardwood stein cuttings.

Root description: Woody to semi-woody. Colored near RHS Brown 200D.

Time to initiate roots: About 4 to 7 weeks at about 27 to 30° C.

Time to produce a rooted young plant: Approximately 9 to 12 weeks in the Summer.

PLANT

Growth habit: Flattened, broad globular, evergreen shrub.

Height: Approximately 60 cm.

Plant spread: Approximately 70 cm.

Branching characteristics: Well branched, approximately 8 lateral branches emerge from a pinch. Smaller lateral branches occurring along main stems. Branches occur at approximately 15° to 75° angles.

Primary branches:

Length of primary branches: Average 10 to 20 cm.

Diameter of primary branches: Average range 4 to 9 mm.

Primary branch strength: Moderately strong.

Primary branch color: Near RHS Grey-Brown 199A.

Primary branch texture: Rough, nearly scaly.

Lateral branches:

*Color*.—New growth near RHS Greyed-Red 180C. Mature growth near Grey-Brown 199D, flushed 179C.

*Length*.—Average range 10 to 35 cm.

*Diameter*.—Approximately 4 mm.

*Aspect*.—Slightly curved.

*Texture*.—Immature slightly pubescent, mature rough, somewhat scabrous.

*Strength*.—Moderately strong, flexible.

*Internode*.—Average range 1.2 cm to 2.3 cm.

Age of plant described: Approximately 2 years.

FOLIAGE

Leaf:

*Type*.—Simple.

*Arrangement*.—Alternate.

*Average length*.—Approximately 4 to 6 cm.

*Average width*.—Approximately 1.5 cm.

*Shape of blade*.—Narrow elliptic.

*Apex*.—Acute.

*Base*.—Attenuate.

*Attachment*.—Sessile.

*Margin*.—Entire.

*Internode*.—Average 0.5 cm.

*Texture of top surface*.—Glabrous.

*Texture of bottom surface*.—Glabrous.

*Appearance of top surface*.—Glossy.

*Appearance of bottom surface*.—Matte.

*Color*.—Young foliage upper side: Near RHS Greyed-Red 178C flushed 181A. Young foliage under side: Near RHS Greyed-Red 178C, apex 178A. Mature foliage upper side: Near RHS Green 139A overlaid with 141A. Mature foliage under side: Near RHS Green 137B.

*Venation*.—Type: Pinnate. Venation color upper side: Near RHS Yellow-Green 144C. Venation color under side: Near RHS Yellow-Green N144D.

FLOWER

Not observed to date.

REPRODUCTIVE ORGANS

Not observed to date.

OTHER CHARACTERISTICS

Disease and pest resistance: Neither resistance nor susceptibility to normal diseases and pests observed.

Temperature tolerance: USDA Zone 7 to 9.

Fruit/seed production: Not observed to date.

What is claimed is:

1. A new and distinct cultivar of *Distylium* plant named 'BLDY02' as herein illustrated and described.

* * * * *